United States Patent [19]

Hattori et al.

[11] 4,444,983
[45] Apr. 24, 1984

[54] PROCESS FOR THE NUCLEAR CHLORINATION OF TOLUENE

[75] Inventors: Ryoji Hattori; Yoshihiko Abe; Sueo Kanno; Satoshi Maeda, all of Kooriyama, Japan

[73] Assignee: Hodogaya Chemical Co., Ltd., Tokyo, Japan

[21] Appl. No.: 368,759

[22] Filed: Apr. 15, 1982

[30] Foreign Application Priority Data

Apr. 21, 1981 [JP] Japan ................................. 56-59101
Apr. 21, 1981 [JP] Japan ................................. 56-59102

[51] Int. Cl.³ ............................................. C07C 17/12
[52] U.S. Cl. ..................................................... 570/209
[58] Field of Search ........................................ 570/209

[56] References Cited

U.S. PATENT DOCUMENTS 4,190,609  2/1980  Lin ........................................ 570/209
4,289,916  9/1981  Nakayama et al. ................. 570/209

FOREIGN PATENT DOCUMENTS 56-5139    of 1981  Japan ................................. 570/209
56-104827  of 1981  Japan ................................. 570/209
56-105752  of 1981  Japan ................................. 570/209
56-110630  of 1981  Japan ................................. 570/209

Primary Examiner—Charles F. Warren
Assistant Examiner—Joseph A. Boska
Attorney, Agent, or Firm—Bucknam and Archer

[57] ABSTRACT

Para-chlorotoluene is prepared selectively at high yield by nuclear chlorination of toluene, in the presence of a Lewis acid catalyst, and a co-catalyst comprising at least one compound selected from the group consisting of phenoxthine derivatives and highly chlorinated phenoxthine derivatives obtained by chlorinating said phenoxthine derivatives at higher degree, said phenoxthine derivatives being represented by the general formula of:

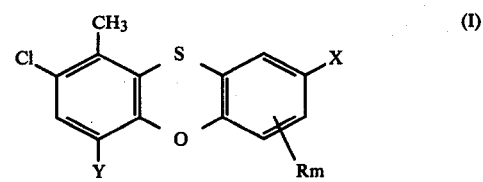

wherein
R represents methyl group or groups at the position-1 and/or position-3,
m is zero or an integer of 1 or 2,
X is hydrogen or chlorine atom, and
Y is chlorine atom or methyl group;

and wherein
m is an integer of 1 or 2 and
X is hydrogen or chlorine atom when Y is chlorine atom,
X is chlorine atom when Y is methyl group and m is zero, and
X is hydrogen atom when Y is methyl group and m is an integer of 1 or 2.

10 Claims, No Drawings

PROCESS FOR THE NUCLEAR CHLORINATION OF TOLUENE

BACKGROUND OF THE INVENTION

1. Field of the Invention

The present invention relates to a process for preparing a chlorinated toluene derivative which is chlorinated at its nuclear position or positions, and particularly relates to a novel co-catalyst which is used in the process for the preparation of a chlorinated toluene to form a product selectively chlorinated at para-position.

2. Brief Description of the Prior Art

Processes for the preparation of nuclearly chlorinated toluenes and the products prepared thereby have been recognized in the art as being extremely important industrial techniques and products. The chlorination reaction has been carried out, most commonly, in the presence of a Lewis acid catalyst such as antimony chloride, ferric chloride or aluminum chloride, to form monochloride and polychlorides and position isomers thereof together with additional formation of benzyl chloride under certain reaction conditions. The main products formed under conditions for the preparation of monochlorotoluene are o-chlorotoluene (hereinafter referred to as OCT) and p-chlorotoluene (hereinafter referred to as PCT), and the by-products include small amounts of m-chlorotoluene (hereinafter referred to as MCT), dichlorotoluene and benzyl chloride, the formation and quantity of the aforementioned by-products varying depending on the reaction conditions employed.

Among the main products, i.e. OCT and PCT, OCT is relatively useless but PCT is a very important industrial product and of high value in a wide range of fields as a material for various industrial products, agricultural chemicals and medical products. For this reason, it is important to increase the yield ratio of PCT to OCT in the preparation of monochlorotoluene from the economical standpoint of view. Any increase in the yield ratio of PCT relative to the total quantity of monochlorotoluene, even a mere 0.5% increase, is of great economic merit. Many efforts have hitherto been made to increase the yield ratio of PCT by selecting suitable catalyst and conditions for chlorination.

For example, U.S. Pat. No. 3,000,975 discloses a process wherein a chloride of titanium, tin or zirconium is used as the catalyst to obtain the result of PCT/OCT=23/75, and U.S. Pat. No. 3,226,447 discloses a process wherein a combined catalyst comprising a halide of iron, aluminum or antimony and an organic sulfur compound, such as mercaptoacetic acid, is used to obtain the result of PCT/OCT=31.5/38.0. Further improved results were obtained by using the catalysts disclosed in the following earlier Patent specifications, these known catalysts including a catalyst system comprising FeCl$_3$ and S$_2$Cl$_2$ as disclosed in Nederland Patent Application No. 6,511,488, a catalyst comprising PtO$_2$ as disclosed in U.S. Pat. No. 3,317,617, a catalyst disclosed in French Pat. No. 1,491,143 which comprises an iron base catalyst combined with a co-catalyst made of an inorganic sulfur compound, such as SOCl$_2$, CS$_2$ or ZnS, and a catalyst disclosed in French Pat. No. 1,491,144 which comprises a Lewis acid catalyst combined with selenium or an organic sulfur compound, such as thiophene or dimethylthiophene.

Referring further to the prior publications, Japanese Patent Publication No. 34009/1975 discloses a catalyst system comprising iron combined with selenium, selenium oxide or selenium halide to obtain the result of PCT/monochlorotoluene=52.1 to 52.6%, Japanese Patent Laid-Open Publication No. 19631/1977 discloses a catalyst comprising a Lewis acid combined with a thianthrene co-catalyst to obtain the result of PCT/monochlorotoluene=50.5%, Japanese Patent Laid-Open Publication No. 19630/1977 discloses a similar catalyst containing polychlorothianthrene to obtain the result of PCT/monochlorotoluene=55.9%, and Japanese Patent Laid-Open Publications No. 44529/1978 and No. 87323/1978 discloses a similar catalyst containing a co-catalyst made of thianthrene compound having an electron attractive substituent and an electron donative substituent to obtain the result of PCT/monochlorotoluene=56 to 59%.

Furthermore, Japanese Patent Laid-Open Publication No. 5139/1981 discloses a phenoxthine compound having a hydrogen atom, an electron attractive group or an electron donor group at the position 2-, 3-, 7-, or 8-.

The yield ratio of PCT to OCT can, in fact, be improved according to the processes disclosed in the prior publications referred to above. However, these known catalyst include those which do not act to increase the yield ratio to the expected extent, which are too expensive to be used in the industrial scale, those containing a co-catalyst which cannot be easily synthesized, and those which can not increase the yield so substantially or which can not be readily available. For such reasons, difficulties are encountered in using them on an industrial scale, even though the selectivity to PCT may be improved satisfactorily by their use.

BRIEF SUMMARY OF THE INVENTION

It is, therefore, the principal object of this invention to provide an improved process in which toluene is nuclearly chlorinated as will be referred to hereinafter throughout this specification and appended claims.

More specifically, the object of this invention is to provide a process for the preparation of monochlorotoluene wherein a co-catalyst having an extremely high selectivity to para-position chlorination is used to produce PCT very effectively and conveniently from the industrial standpoint.

We have already accomplished an invention relating to a process for the preparation of chlorinated toluene wherein a co-catalyst comprising a halogenated phenoxthine compound having an alkyl substituent or no substituent, and have filed a Patent Application (Japanese Patent Application No. 1350/1980 published as Japanese Patent Laid-Open Publication No. 110630/1981). Through further studies, it was found that certain phenoxthine compounds obtained from specific diphenylethers and chlorinated derivatives of the aforementioned certain phenoxthines obtained by further chlorinating them have extremely active promotive actions especially when used for chlorinating toluene at low temperature to give the results of distinctively high selectivity to para-position chlorination. This invention is based on the aforementioned finding.

More specifically, the process for the nuclear chlorination of toluene using a Lewis acid catalyst according to this invention is characterized by the use of a co-catalyst comprising at least one compound selected from the group consisting of phenoxthine derivatives and highly chlorinated phenoxthine derivatives obtained by chlorinating said phenoxthine derivatives at higher degree, said phenoxthine derivatives being represented by the general formula of:

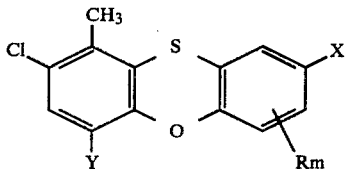

(I)

wherein
R represents methyl group or groups at the position-1 and/or position-3,
m is zero or an integer of 1 or 2,
X is hydrogen or chlorine atom, and
Y is chlorine atom or methyl group;
and wherein
m is an integer of 1 or 2 and
X is hydrogen or chlorine atom when Y is chlorine atom,
X is chlorine atom when Y is methyl group and m is zero, and
X is hydrogen atom when Y is methyl group and m is an integer of 1 or 2.

DETAILED DESCRIPTION OF THE PREFERRED EMBODIMENTS

The main component of the catalyst composition according to this invention is a Lewis acid, and various known Lewis acids currently used as catalysts may be conveniently used in the present invention. Substances forming Lewis acids or exhibiting similar actions during the chlorination reaction may also be used. General examples of such a Lewis acid include elementary antimony and iron; halides, oxyhalides, oxides, sulfides, and carbonyl compounds of antimony, iron aluminum, tin and titanium; and organometallic compounds of the aforementioned metals. Representative examples are antimony trichloride, antimony pentachloride, antimony trioxide, antimony oxychloride, ferric chloride, iron sulfide, aluminum chloride and tin tetrachloride, antimony trichloride, antimony pentachloride and ferric chloride being particularly preferred.

Specific examples of the phenoxthine compounds used in this invention and represented by the general formula (I) wherein Y is chlorine atom (these compounds being hereinafter referred to as PX Compound of Group-A) include 3,9-dimethyl-6,8-dichlorophenoxthine, 3,9-dimethyl-2,6,8-trichlorophenoxthine, 1,3,9-trimethyl-6,8-dichlorophenoxthine and 1,3,9-trimethyl-2,6,8-trichlorophenoxthine.

Specific examples of the phenoxthine compounds represented by the general formula (I) wherein Y is methyl group (these compounds being hereinafter referred to as PX Compound of Group-B) include 6,9-dimethyl-2,8-dichlorophenoxthine, 3,6,9-trimethyl-8-chlorophenoxthine and 1,3,6,9-tetramethyl-8-chlorophenoxthine.

The former two compounds of the four PX Compounds of Group-A include isomers, 1,9-dimethyl-6,8-dichlorophenoxthine and 1,9-dimethyl-2,6,8-trichlorophenoxthine having methyl groups at their peri-positions relative to the S atom and obtained by the cyclization reaction by sulfur, as suitable compounds which may be used in this invention. Similarly, the compound belonging to the PX Compound of Group-B wherein m of $R_m$ group takes the value of 1, namely 3-methyl-compound, forms 1,6,9-trimethyl-8-chlorophenoxthine having methyl groups at its peri-positions relative to the S atom during the cyclization reaction by sulfur, and such a compound is included as a compound which may be used as the co-catalyst in the process of this invention.

Now, an example of a process for preparing an PX Compound of Group-A used as the co-catalyst in this invention will be described below. 2,4-dichlorotoluene is brominated to obtain 5-bromo-2,4-dichlorotoluene which is then reacted with a substituted phenol, such as 3,5-xylenol, compatible with the PX Compound of Group-A generally in accordance with the method described in "Lectures on Chemical Experiment (JIKKEN KAGAKU KOZA)" Vol. 19, page 182 or described in Chemical Abstracts, Vol. 65, 10530f (1966) or other papers. Then, the fraction of 5,3',5'-trimethyl-2,4-dichlorodiphenylether is separated by distillation under reduced pressure. The thus obtained 5,3',5'-trimethyl-2,4-dichlorodiphenylether is reacted with sulfur or sulfur chloride in the presence of an aluminum chloride catalyst generally in accordance with the method described in Organic Syntheses Col. Vol., Vol. 2, page 485, whereby 1,3,9-trimethyl-6,8-dichlorophenoxthine is synthesized.

Similarly, the PX Compound of Group-B may be synthesized by the steps of brominating 2-chloro-p-xylene to obtain 2-chloro-5-bromo-p-xylene from which 2,5,3'-trimethyl-4-chlorodiphenylether is synthesized, followed by preparing 1,6,9-trimethyl-8-chlorophenoxthine or 3,6,9-trimethyl-8-chlorophenoxthine.

In order to chlorinate the aforementioned phenoxthine compounds at higher degree, the phenoxthine compounds are chlorinated in the presence of a Lewis acid catalyst while using an inert solvent, such as nitrobenzene, if necessary. The amount of the Lewis acid catalyst used should be in the range of from 0.001 to 5% based on the phenoxthine compounds, and chlorine is introduced in an amount equal to or in excess of the stoichiometric amount required for the desired degree of chlorination at a temperature of from 50° C. to 150° C., preferably at 70° C. to 120° C. to obtain a chlorinated phenoxthine compound having the desired degree of chlorination. By the use of a highly chlorinated compound, the function of co-catalyst can be enhanced as compared to the corresponding phenoxthine compound which has not been chlorinated to higher degree of chlorination. However, the product prepared through the steps of synthesizing 1,3,9-trimethyl-8-chlorophenoxthine having no substituent at its 6-position followed by a further chlorination, for example, did not exhibit a promotive action having high para-selectivity as obtainable in the present invention, although it was estimated that a product resembling the phenoxthine compounds used in this invention was prepared.

In view of the above, the essential conditions required for the PX Compound of Group-A prior to chlorination to form a co-catalyst having excellent promoting action, according to this invention, are that methyl group or groups be present at the position-1 and/or position-3 of 9-methyl-6,8-dichlorophenoxthine, and that hydrogen atom or chlorine atom be present at the position-2. Simlarly, in order to obtain a co-catalyst having excellent promoting property to form chlorinated toluene at high para-selectivity, the PK Compound of Group-B prior to chlorination must have methyl group or groups at the position-1 and/or position-3 of the 6,9-dimethyl-8-chlorophenoxthine, or must have chlorine atom at the position-2 when the compound does not have the said methyl group.

Total number of the substituting chlorine atoms contained in the chlorinated phenoxthine derived from the PX Compound of Group-A ranges within 2 to 6, and appreciably effective function may be obtained where the total number ranges from 3 to 5. On the other hand, total number of the substituting chlorine atoms contained in the chlorinated phenoxthine derived from the PX Compound of Group-B ranges between 1 and 5, and appreciably effective function may be obtained where total number is between 1 and 4. The advantageous effect according to this invention may be obtained when a mixture of the chlorinated products each having a different number of substituting chlorine atoms, namely each having a different degree of chlorination, is used. It is, therefore, intended to include such a mixture in the broad scope of the claims of this application.

The quantities of the main catalyst and the co-catalyst used may be varied within a relatively wide range. The amount of the main catalyst, a Lewis acid, should be between about 0.005 wt% and about 5%, based on the weight of toluene, and the ratio by weight of the co-catalyst to the main catalyst may range from 0.05:1 to 20:1. It is preferred that the amount of the main catalyst be about 0.01 wt% to about 1 wt% based on the weight of toluene and the ratio by weight of the co-catalyst to the main catalyst be from 0.2:1 to 5:1, in order to increase the yield ratio of PCT to the utmost level and also in view of economy.

The chlorination process according to this invention wherein the main catalyst and the co-catalyst are as described above and defined in the appended claims, may be carried out at a reaction temperature of from below 0° C. to the boiling point. Generally, the reaction temperature may be set between 0° C. and 80° C. However, it is preferred that the process of this invention be carried out at a temperature of from 0° C. to 40° C., since the co-catalyst provided by this invention exhibits high selectivity to the para-position at lower temperature.

Although the process of this invention may be effected in a reaction system operated under increased or reduced pressure, it is recommended that the process be carried out at atmospheric pressure. The process may be effected in the presence of a solvent. However, the presence of solvent is not essential. The process may be carried out in a batch system or through a continuous operation.

The yield ratio of PCT to OCT of the product prepared in accordance with the process of this invention is well over 1.1. When calculated as the yield ratio of PCT to all monochlorotoluene products, this yield ratio corresponds to 52% and, under certain conditions, over 60%, which are exceedingly higher than obtainable by any of the known processes. Further advantages obtained by the use of the co-catalyst according to this invention are that the quantities of by-products, such as MCT, other than PCT and OCT are decreased, and that the quantity of the by-product benzyl chloride can also be minimized to a negligile level by selecting optimum reaction conditions. Furthermore, the co-catalyst may be easily prepared by any of the known methods. Finally, the co-catalyst according to this invention is well suited for the production of PCT efficiently on an industrial scale. It is believed that the present invention will make an important contribution to chemical industries using PCT.

The present invention will now be described more specifically with reference to Examples thereof. In the following Examples, "part" stands for "part by weight" unless otherwise specified.

REFERENCE EXAMPLE 1

Synthesis of 2,4-Dichloro-5-bromotoluene 500 parts of 2,4-dichlorotoluene (b.p.=198° to 200° C.) and 10 parts of anhydrous aluminum chloride were charged into a 1-liter four-necked flask provided with a reflux condenser, a thermometer, a stirrer and a dropping funnel. 397 parts of bromine was added dropwisely at 30° to 40° C. over a period of 5 hours. The reaction liquid was washed with warm water followed by separating the water layer, and then the oil layer was cooled. The separated crystals were filtered off, recrystallized from methanol to obtain 295 parts of 2,4-dichloro-5-bromotoluene having a melting point of 82.5° to 84.0° C.

REFERENCE EXAMPLE 2

Synthesis of 3,5'-Dimethyl-4,2',4'-trichlorodiphenylether

Into a 300 ml volume four-necked flask provided with a reflux condenser, a thermometer, a stirrer and a dropping funnel, were charged a reaction product of 69 parts of p-chloro-m-cresol with caustic potassium, 115 parts of 2,4-dichloro-5-bromotoluene prepared by Reference Examples 1, 2 parts of potassium iodide, and 0.5 part of copper powder, and the reaction was continued at 170° to 200° C. for 10 hours. After the completion of the reaction, 100 ml of toluene was added to the reaction liquid followed by filtration for removing insoluble ingredients, and then the oil layer was washed with dilute aqueous solution of caustic soda and water, respectively, one time each. Then, the washed oil layer was separated and distilled under reduced pressure to obtain 72 parts of a fraction of 188° to 193° C./7 mmHg of 3,5'-dimethyl-4,2',4'-trichlorodiphenylether.

REFERENCE EXAMPLE 3

Synthesis of 3,9-Dimethyl-2,6,8-trichlorophenoxthine

A dropping funnel was attached to the aforementioned four-necked flask into which 60 parts of 3,5'-dimethyl-4,2',4'-trichlorodiphenylether and 4 parts of granular aluminum chloride were charged, and 27.6 parts of sulfur chloride was dropwisely added thereto at 50° to 80° C. over a period of 3 hours. After the completion of the reaction, 100 ml of water and 80 ml of 1,2-dichloroethane were added to the reaction liquid. The fraction dissolved in the dichloroethane was separated, and then the fraction was concentrated under reduced pressure by distilling dichloroethane off. The concentrated product was recrystallized from acetone to obtain 47 parts of 3,9-dimethyl-2,6,8-trichlorophenoxthine having a melting point of 127° to 142° C.

REFERENCE EXAMPLE 4

Synthesis of Chlorinated 3,9-Dimethyl-2,6,8-trichlorophenoxthine

Into a four-necked flask similar to that used in the preceding examples except that an inlet tube for introducing chlorine was provided in place of the dropping funnel, 37 parts of the 3,9-dimethyl-2,6,8-trichlorophenoxthine prepared according to Reference Example 3, 36 parts of nitrobenzene and 0.5 part of antimony pentachloride were charged. The temperature in the flask was maintained at 90° to 110° C. to effect chlorination at the chlorine introduction rate of 0.2 to 0.3 part/min. to synthesize chlorinated 3,9-dimethyl-2,6,8-trichlorophenoxthine (hereinafter referred to as chlorinated 3,9-dimethyl-2,6,8-trichloro-PX).

The chlorinated reaction liquid was exposed to nitrogen gas, and then added with toluene and a large quantity of methanol. The separate crystals were filtered and dried, and used as the co-catalyst.

Inorganic ingredients contained in each of the synthesized samples were removed by washing treatment, and the thus obtained sample deprived of the inorganic ingredients was subjected to analysis to learn the average chlorine content.

REFERENCE EXAMPLE 5

Synthesis of 2-Chloro-5-bromo-p-xylene 400 parts of 2-chloro-p-xylene (b.p.=183° to 184° C.) and 2 parts of anhydrous aluminum chloride were charged into a 1-liter four-necked flask provided with a reflux condenser, a thermometer, a stirrer and a dropping funnel, to which 360 parts of bromine was dropwisely added over a period of 5 hours to carry out the reaction at 35° to 60° C. Water was added to the reaction liquid to wash the same with the thus added water and to remove the catalyst, and then the oil layer was cooled. The separated crystals were filtered, and washed with methanol to obtain 377 parts of 2-chloro-5-bromo-p-xylene having a melting point of 60° to 64° C.

REFERENCE EXAMPLE 6

Synthesis of 2,5,3'-trimethyl-4-chlorodiphenylether

Into a 300 ml volume four-necked flask provided with reflux condenser, a thermometer and a stirrer were charged a reaction product of 45 parts of m-cresol and caustic potassium, 80 parts of 2-chloro-5-bromo-p-xylene prepared according to Reference Example 5, 2 parts of potassium iodide, and 0.5 part of copper powder. The reaction was carried out at 170° to 200° C. for 10 hours. After being added with 100 ml of toluene, the reaction liquid was filtered to remove insoluble matters, and then the oil layer was washed with a dilute aqueous solution of caustic soda and water, one time each. After separation, the oil layer was distilled under reduced pressure to obtain 58 parts of a fraction of 163° to 170° C./4 mmHg of 2,5,3'-trimehtyl-4-chlorodiphenylether.

REFERENCE EXAMPLE 7

Synthesis of 3,6,9-Trimethyl-8-chlorophenoxthine

A dropping funnel was attached to the aforementioned four-necked flask into which 40 parts of 2,5,3'-trimethyl-4-chlorodiphenylether and 2 parts of granular aluminum chloride, and 15.2 parts of sulfur chloride was dropwisely added thereto at 50° to 90° C. over a period of about 3 hours. After the completion of the reaction, 100 ml of water and 80 ml of dichloroethane were added to the reaction liquid, and the fraction dissolved in dichloroethane was separately taken out. Dichloroethane was distilled off from the fraction, and the fraction was subjected further to distillation under reduced pressure to obtain a viscous raw product of 3,6,9-trimethyl-8-chlorophenoxthine.

REFERENCE EXAMPLE 8

Synthesis of 3,6,9-Trimethyl-8-chlorophenoxthine 30 parts of the raw product of the phenoxthine compound prepared according to the preceding Reference Example 7 was charged into a similar four-necked flask provided with an inlet tube for introducing chlorine in place of the dropping funnel. 36 parts of nitrobenzene and 0.5 part of antimony pentachloride were added, and then chlorination was effected at an inner temperature of 90° to 110° C. and at a flow rate of chlorine of 0.2 to 0.4 part/min. to synthesize chlorinated products of 3,6,9-trimethyl-8-chlorophenoxthine (hereinafter referred to as 3,6,9-trimethyl-8-chloro-PX) having different degrees of chlorination.

The chlorinated reaction liquid was exposed to nitrogen gas, and then added with a small quantity of toluene and a large quantity of methanol. The separated crystals were filtered and dried, and used as the co-catalyst. Each of the samples was separately subjected to washing treatment to remove inorganic ingredients sufficiently, and then each sample was subjected to analysis to learn the average chlorine content.

EXAMPLES 1 AND 2

The reactor used for the chlorination of toluene was a tubular glass vessel having a diameter of 40 mm and a length of 500 mm, and a thermometer, a reflux condenser, and an inlet tube for introducing chlorine were attached thereto. The charged quantity of toluene was 460 ml, to which 500 ppm of antimony trichloride was added as the main catalyst component. As the co-catalyst, 500 ppm of 3,9-dimethyl-2,6,8-trichlorophenoxthine or the chlorinated 3,9-dimethyl-2,6,8-trichloro-PX prepared, respectively, by Reference Examples 3 and 4, were used to chlorinate toluene at a flow rate of chlorine of 1.2 parts/min.

The results are shown in Table 1. Examples 1 and 2 are experiments wherein the degree of chlorination of the phenoxthine compounds used as the co-catalyst are changed, namely the chlorine contents are varied. The compositions of the reaction liquids set forth in the following Tables are the results of quantitative analysis conducted by using gas chromatography.

COMPARATIVE EXAMPLES 1 TO 4

Various phenoxthine compounds were synthesized in accordance with procedures similar to the processes as described in Reference Examples 1 to 4, and the obtained products were further chlorinated. The chlorinated products were used as the co-catalysts and the promotive actions thereof were compared with those of the co-catalysts according to this invention. The results are shown also in Table 1 as Comparative Examples 1 and 2. The promotive action of 2,3,7,8-tetrachlorophenoxthine and that of 3-methyl-2,7,8-trichlorophenoxthine are also shown in Table 1, as Comparative Examples 3 and 4. The conditions for the chlorination of toluene were the same as in Examples 1 and 2. The chemical structures and the properties of the substituted diphenylether used as the starting materials are also shown.

In the Table, the average chlorine content of the co-catalyst means the total number of substituting chlorine atoms, and the average number calculated from the result of the analysis of chlorine determined in accordance with the method described in the preceding Reference Example 4.

ppm. Using antimony trichloride as the main catalyst component in an amount of 500 ppm, similar to Exam-

TABLE 1

| Starting Diphenylether | | Boiling Point °C./ mmHg | Co-catalyst Compounds | Chloration Reaction | | | | | | PCT/ Monochlorotoluene % |
|---|---|---|---|---|---|---|---|---|---|---|
| | | | | Average Chlorine Content | Reaction Temperature °C. | Chlorination Degree | Composition of Reaction Liquid % | | | |
| | | | | | | | Toluene | OCT | PCT | Dichlorotoluene |
| Example 1 | [structure: 3,9-dimethyl-2,6,8-trichloro-PX, with CH3, Cl groups] | 188–193/7 | 3,9-Dimethyl-2,6,8-trichloro-PX | 3.0 | 35 | 0.98 | 2.6 | 45.7 | 51.5 | 0.2 | 53.0 |
| Example 2 | [structure] | 188–193/7 | Chlorinated 3,9-Dimethyl-2,6,8-trichloro-PX | 4.3 | 35 | 0.88 | 11.9 | 38.3 | 49.8 | 0 | 56.5 |
| Comparative Example 1 | [structure] | 183–186/7 | Chlorinated 3,9-Dimethyl-2,8-dichloro-PX | 4.9 | 35 | 0.96 | 3.9 | 44.5 | 51.4 | 0.2 | 53.6 |
| Comparative Example 2 | [structure] | 154–158/6 | Chlorinated 3-Methyl-2-chloro-PX | 4.6 | 35 | 0.94 | 5.9 | 46.6 | 47.2 | 0.3 | 50.3 |
| Comparative Example 3 | [structure] | mp 58–60° C. | 2,3,7,8-Tetrachloro-PX | 4.0 | 35 | 0.85 | 15.2 | 39.9 | 44.9 | 0 | 52.9 |
| Comparative Example 4 | [structure] | (Oily Product) | 3-Methyl-2,7,8-trichloro-PX | 3.0 | 35 | 0.96 | 4.4 | 45.2 | 50.1 | 0.3 | 52.6 |

Note:
"PX" represents "Phenoxthine".

It should be understood from the results shown in Table 1 that regarding the 3,9-dimethyl-2,6,8-trichlorophenoxthine a derivative having a higher average chlorine content and obtained by further chlorinating the said compound (Example 2) has a higher selectivity to para-position. Comparing this Example with Comparative Example 1, it is clear that the selectivity to PCT varies considerably depending on the presence or absence of preliminarily introduced substituting chlorine at the position-6 even if the otherwise same chlorinated 3,9-dimethyl-PX compounds are used. From a comparison with Comparative Examples 2 to 4, it is clear that the respective substituting groups represented by "9-methyl-6,8-dichloro-" are essential for attaining high para-selectivity.

EXAMPLE 3

Following the process described in Reference Examples 1 to 4, 1,3,9-trimethyl-6,8-dichlorophenoxthine was synthesized from 3,5-xylenol, and then chlorinated to obtain 1,3,9-trimethyl-6,8-dichlorophenoxthine (hereinafter referred to as 1,3,9-trimethyl-6,8-dichloro-PX) which was used as a co-catalyst in an amount of 500 ples 1 and 2, toluene was chlorinated. The results are shown in Table 2.

EXAMPLE 4

Toluene was chlorinated according to a similar procedure to that in Examples 1 and 2, except in that a 1:1 mixture of the chlorinated 3,9-dimethyl-2,6,8-trichloro-PX as used in Example 2 and the chlorinated 1,3,9-trimethyl-6,8-dichloro-PX as used in Example 3 was used as the co-catalyst. The results are shown in Table 2.

COMPARATIVE EXAMPLES 5 TO 7

Generally in accordance with the processes as described in Reference Examples 1 to 4, a variety of chlorinated phenoxthine compounds were synthesized from the corresponding different substituted diphenylethers. The obtained chlorinated phenoxthine compounds were used as the co-catalysts, and in the processes for chlorinating toluene, similarly as in Examples 1 and 2. The results are shown in Table 2 for the purpose of comparison with the results obtainable by the present invention.

TABLE 2

| | Starting Diphenylether | | Co-catalyst | | Chlorination Reaction | | | | | | PCT/ Monochlorotoluene % |
|---|---|---|---|---|---|---|---|---|---|---|---|
| | | Boiling Point °C./ mmHg | Compounds | Average Chlorine Content | Reaction Temperature °C. | Chlorination Degree | Composition of Reaction Liquid % | | | | |
| | | | | | | | Toluene | OCT | PCT | Dichlorotoluene | |
| Example 3 | (structure) | 186–197/3 | Chlorinated 1,3,9-Trimethyl-6,8-dichloro-PX | 4.4 | 35 | 1.01 | 0.1 | 43.9 | 55.1 | 0.9 | 55.7 |
| Example 4 | (structure) | | Chlorinated 1,3,9-Trimethyl-6,8-dichloro-PX 250ppm | 4.4 | 35 | 0.96 | 4.6 | 41.7 | 53.5 | 0.2 | 56.2 |
| | (structure) | | Chlorinated 3,9-Dimethyl-2,6,8-trichloro-PX 250ppm | 4.3 | | | | | | | |
| Comparative Example 5 | (structure) | 174–177/7 | 1,3,9-Trimethyl-8-chloro-PX | 3.9 | 35 | 0.98 | 2.1 | 45.7 | 51.9 | 0.3 | 53.2 |
| Comparative Example 6 | (structure) | 180–183/5 | Chlorinated 9-Methyl-2,6,8-trichloro-PX | 4.2 | 35 | 0.96 | 4.3 | 44.8 | 50.5 | 0.4 | 53.0 |
| Comparative Example 7 | (structure) | 142–154/3 | Chlorinated 3,6-Dimethyl-9-chloro-PX | 5.0 | 35 | 0.97 | 3.8 | 45.5 | 50.3 | 0.4 | 52.5 |

Note:
"PX" represents "Phenoxthine".

It should be clear, from the results shown in Table 2, that the phenoxthine compounds included in this invention must have the substituting groups represented by "9-methyl-6,8-dichloro-" and other additional specific substituting groups. It is also clear that these phenoxthine compounds exhibit extremely high promotive actions even when used in the form of a mixture.

EXAMPLES 5 AND 6

Generally in accordance with the procedures as described in Reference Examples 1 and 2, 3,5′-dimethyl-2′,4′-dichorodiphenylether (b.p.=161° to 171° C./3 mmHg) was synthesized from m-cresol, and then converted into 3,9-dimethyl-6,8-dichlorophenoxthine similarly as in Reference Example 3 followed by chlorination, in accordance with the procedure as set forth in Reference Example 4, to prepare chlorinated 3,9-dimethyl-6,8-dichlorophenoxthine (hereinafter referred to as 3,9-dimethyl-6,8-dichloro-PX) which was used as the co-catalyst. Toluene was chlorinated similarly by as in Examples 1 and 2, except in that the reaction temperatures were changed to 35° C. and 20° C., respectively, while using $SbCl_5$ as the main catalyst component. The results are shown in Table 3. The yield ratio of m-chlorotoluene, which was difficult to separate from PCT, was determined by gas chromatography under different analysis conditions to fine that the yield ratio of m-chlorotoluene to PCT was about 0.4% in the case of Example 6. The yield ratio of benzyl chloride contained in the reaction liquid was below the detectable value.

EXAMPLE 7

Toluene was chlorinated at 40° C. while using the same co-catalyst as used in Examples 5 and 6 and using ferric chloride as the main catalyst component. The results are shown in Table 3.

COMPARATIVE EXAMPLES 8 TO 10

Using the chlorinated 3-methyl-PX as the co-catalyst, toluene was chlorinated in the manner similar to Examples 5, 6 and 7 to obtain the data which were to be compared with the data obtained by Examples 5, 6 and 7. The result of these Comparative Examples are shown in Table 3.

TABLE 3

| | Main Catalyst Component | | Co-catalyst | | | Chlorination Reaction | | | | | | PCT/Mono chlorotolene % |
|---|---|---|---|---|---|---|---|---|---|---|---|---|
| | | | | Average Chlorine Content | ppm | Temp. °C. | Chlorination Degree | Composition of Reaction Liquid % | | | | |
| | Compounds | ppm | Compounds | | | | | Toluene | OCT | PCT | Dichlorotoluene | |
| Example 5 | SbCl$_5$ | 500 | Chlorinated 3,9-Dimethyl 6,8-dichloro-PX | 5.1 | 500 | 35 | 0.97 | 3.1 | 42.3 | 54.4 | 0.2 | 56.3 |
| Example 6 | SbCl$_5$ | 500 | Chlorinated 3,9-Dimethyl 6,8-dichloro-PX | 5.1 | 500 | 20 | 0.98 | 2.1 | 40.2 | 57.2 | 0.5 | 58.7 |
| Example 7 | FeCl$_3$ | 500 | Chlorinated 3,9-Dimethyl 6,8-dichloro-PX | 5.1 | 500 | 40 | 0.99 | 1.3 | 45.3 | 52.8 | 0.6 | 53.8 |
| Comparative Example 8 | SbCl$_5$ | 500 | Chlorinated 3-Methyl-PX | 4.9 | 500 | 35 | 0.97 | 3.5 | 43.2 | 53.0 | 0.3 | 55.1 |
| Comparative Example 9 | SbCl$_5$ | 500 | Chlorinated 3-Methyl-PX | 4.9 | 500 | 20 | 0.95 | 4.7 | 41.3 | 53.9 | 0.1 | 56.6 |
| Comparative Example 10 | FeCl$_3$ | 500 | Chlorinated 3-Methyl-PX | 4.9 | 500 | 40 | 0.99 | 1.4 | 46.1 | 51.8 | 0.7 | 52.9 |

Note:
"PX" represents "Phenoxthine".

From the results of Examples 5 to 7 and Comparative Examples 8 to 10 shown in Table 3, it is apparent that the co-catalyst according to this invention give the results obtainable by the examples of Japanese Patent Application No. 1350/1980 (Japanese Patent Laid-Open Publication No. 110630/1981) with additional remarked increase in para-selectivity when used in chlorination at low temperature.

EXAMPLES 8 AND 9

The reactor used for the chlorination of toluene was a tubular glass vessel having a diameter of 40 mm and a length of 500 mm, and a thermometer, a reflux condenser and an inlet tube for introducing chlorine were attached thereto. The charged quantity of toluene was 460 ml, to which 500 ppm of antimony trichloride was added as the main catalyst component. As the co-catalyst, 500 ppm of the chlorinated 3,6,9-trimethyl-8-chloro-PX prepared by preceding Reference Example 8 was used to chlorinate toluene at a flow rate of chlorine of 1.2 part/min.

The results are shown in Table 4. Examples 8 and 9 are experiments wherein the average chlorine contents contained in respective phenoxthine compounds set forth in Reference Example 8 were varied. The compositions of the reaction liquids set forth in the following Tables are the results of quantitative analysis conducted by using gas chromatography.

The average chlorine content means the total number of substituting chlorine atoms, and obtained by averaging the analytical results of the tests described in said Reference Example 8.

The yield ratio of m-chlorotoluene, which was difficult to separate from PCT, was determined under different analysis conditions to obtain the result that yield ratio thereof to PCT in Example 9 was about 0.4%. In Example 9, the yield ratio of benzyl chloride contained in the reaction liquid was below the detectable value.

COMPARATIVE EXAMPLES 11 TO 15

Various phenoxthine compounds were synthesized in accordance with procedures similar to the processes as described in Reference Examples 5 to 8, and the obtained products were further chlorinated. The chlorinated products were used as the co-catalysts and the promotive actions thereof were compared to those of the co-catalyst according to this invention. The results are shown in Table 4 as Comparative Examples 11 to 13. The promotive action of 2,3,7,8-tetrachlorophenoxthine and that of 3-methyl-2,7,8-trichlorophenoxthine are also shown in Table 4, as Comparative Examples 14 and 15. The conditions for the chlorination of toluene were the same as in Examples 8 and 9. The chemical structures and the properties of the substituted diphenylether used as the starting material are also shown in Table 4.

TABLE 4

| | Starting Diphenylether | Boiling Point °C./mmHg | Co-catalyst Compounds | Average Chlorine Content | Chlorination Reaction | | | Composition of Reaction Liquid % | | | | PCT/Mono-chlorotoluene % |
|---|---|---|---|---|---|---|---|---|---|---|---|---|
| | | | | | Reaction Temperature °C. | Chlorination Degree | Toluene | OCT | PCT | Dichlorotoluene | | |
| Example 8 | Cl-(CH$_3$)-C$_6$H$_2$(CH$_3$)-O-C$_6$H$_4$-CH$_3$ | 163–170/4 | Chlorinated 3,6,9-Trimethyl-8-chloro-PX | 1.4 | 35 | 0.99 | 1.4 | 40.1 | 58.1 | 0.4 | | 59.2 |

TABLE 4-continued

| | Starting Diphenylether | Boiling Point °C./mmHg | Co-catalyst Compounds | Average Chlorine Content | Chlorination Reaction Reaction Temperature °C. | Chlorination Degree | Composition of Reaction Liquid % Toluene | OCT | PCT | Dichlorotoluene | PCT/Monochlorotoluene % |
|---|---|---|---|---|---|---|---|---|---|---|---|
| Example 9 | (structure: Cl, CH3, CH3, CH3 diphenyl ether) | 163–170/4 | Chlorinated 3,6,9-Trimethyl-8-chloro-PX | 2.0 | 35 | 0.98 | 2.0 | 39.3 | 58.3 | 0.4 | 59.7 |
| Comparative Example 11 | (structure: Cl, Cl, CH3, CH3 diphenyl ether) | 142–154/3 | Chlorinated 3,6-Dimethyl-9-chloro-PX | 5.0 | 35 | 0.96 | 3.9 | 45.6 | 50.4 | 0.1 | 52.5 |
| Comparative Example 12 | (structure: Cl, CH3, CH3, Cl, CH3 diphenyl ether) | 182–190/6 | Chlorinated 3,6,9-Trimethyl-2,8-dichloro-PX | 3.7 | 35 | 1.02 | 0 | 45.1 | 52.5 | 2.4 | 53.8 |
| Comparative Example 13 | (structure: Cl, CH3, CH3, CH3, CH3 diphenyl ether) | 162–170/7 | Chlorinated 1,4,6,9-Tetramethyl-8-chloro-PX | 2.1 | 35 | 1.01 | 0.1 | 47.4 | 51.4 | 1.1 | 52.0 |
| Comparative Example 14 | (structure: Cl, Cl, Cl, Cl diphenyl ether) | mp 58–60 C. | 2,3,7,8-Tetrachloro-PX | 4.0 | 35 | 0.85 | 15.2 | 39.9 | 44.9 | 0 | 52.9 |
| Comparative Example 15 | (structure: Cl, Cl, Cl, CH3 diphenyl ether) | (Oily Product) | 3-Methyl-2,7,8-trichloro-PX | 3.0 | 35 | 0.96 | 4.4 | 45.2 | 50.1 | 0.3 | 52.6 |

Note:
"PX" represents "Phenoxthine".

It is clear, from Table 4, by comparing the results of Examples 8 and 9 with those of Comparative Examples 11 to 13, that the substituting groups represented by "6,9-dimethyl-8-chloro-" are essential and that the functional effects of the co-catalysts vary greatly depending on the presence or absence of the X- and R-groups and also on the positions thereof. It should also apparent, while reviewing Comparative Examples 14 and 15, that the para-selectivity of the co-catalyst according to this invention is surprisingly improved over the known co-catalysts when used for the chlorination of toluene.

EXAMPLES 10 TO 13

Generally following the processes as described in Reference Examples 5 to 8, 2,5-dimethyl-4,4'-dichlorodiphenylether and 2,5,3',5'-tetramethyl-4-chlorodiphenylether were synthesized, and then converted into 6,9-dimethyl-2,8-dichlorophenoxthine and 1,3,6,9-tetramethyl-8-chlorophenoxthine, respectively, which were further chlorinated to be used as co-catalysts. The results of the experiments wherein toluene was chlorinated using these co-catalysts while following the general procedure as set forth in Examples 5 and 6 are shown in Table 5.

COMPARATIVE EXAMPLE 16

In order to learn the promotive actions compared to those of the co-catalysts included in this invention, chlorinated, 1,3,9-trimethyl-8-chloro-PX was synthesized generally in accordance with the procedures described in Reference Examples 5 to 8. The thus obtained co-catalyst was used in a process for the chlorination of toluene, the process being carried out similarly to Examples 8 and 9. The results are shown in Table 5.

TABLE 5

| | Starting Diphenylether | Boiling Point °C./mmHg | Co-catalyst Compounds | Average Chlorine Content | Chlorination Reaction Reaction Tempera-ture °C. | Chlori-nation Degree | Composition of Reaction Liquid % Tol-uene | OCT | PCT | Di-chloro-toluene | PCT/Mono-chloro-toluene % |
|---|---|---|---|---|---|---|---|---|---|---|---|
| Example 10 | (structure: Cl, CH₃, CH₃, O, Cl) | 189–190/6 | Chlorinated 6,9-Dimethyl 2,8-dichloro-PX | 3.5 | 35 | 0.93 | 7.5 | 39.9 | 52.2 | 0.4 | 56.7 |
| Example 11 | (structure: Cl, CH₃, CH₃, O, Cl) | 189–190/6 | Chlorinated 6,9-Dimethyl-2,8-dichloro-PX | 3.5 | 20 | 0.98 | 2.1 | 40.1 | 57.5 | 0.3 | 58.9 |
| Example 12 | (structure: Cl, CH₃, CH₃, O, CH₃, CH₃) | 192–198/6 | Chlorinated 1,3,6,9-Tetramethyl-8-chloro-PX | 2.6 | 35 | 0.97 | 3.3 | 42.3 | 54.1 | 0.3 | 56.1 |
| Example 13 | (structure: Cl, CH₃, CH₃, O, Cl) | | Chlorinated 6,9-Dimethyl-2,8-dichloro-PX 250ppm | 3.5 | 30 | 0.98 | 1.9 | 41.5 | 56.3 | 0.3 | 57.6 |
| | (structure: Cl, CH₃, CH₃, O, CH₃, CH₃) | | Chlorinated 1,3,6,9-Tetramethyl-8-chloro-PX 250ppm | 2.6 | | | | | | | |
| Comparative Example 16 | (structure: Cl, CH₃, CH₃, O, CH₃) | 174–177/7 | Chlorinated 1,3,9-Trimethyl-8-chloro-PX | 3.0 | 35 | 0.98 | 2.1 | 45.3 | 52.3 | 0.3 | 53.6 |

Note:
"PX" represents "Phenoxthine".

Comparing the results of Example 12 with those of Comparative Example 16, it is clear that the selectivity to PCT is appreciably different depending on the presence or absence of a specific substituting group as defined in the appended claim, such as methyl group at the position-6. It has been also found that the co-catalysts of this invention act more effectively at lower temperature as shown by Examples 10 and 11, and that the phenoxthine compounds show high para-selectivity even if used in the form of a mixture.

EXAMPLES 14 TO 17

Generally following the procedures as set forth in Reference Examples 5 to 8, 3,6,9-trimethyl-8-chlorophenoxthine was synthesized, and then chlorinated to obtain chlorinated 3,6,9-trimethyl-8-chloro-PX which was used as the co-catalyst. Toluene was chlorinated generally similarly to the manner described in Examples 8 and 9, except in that the added quantity of the aforementioned co-catalyst, the average chlorine content of the co-catalyst, the specific kind of the used main catalyst component and the reaction temperature were varied. The results thus obtained are shown in Table 6.

COMPARATIVE EXAMPLES 17 TO 19

Generally following the procedures as described in Reference Examples 5 to 8, chlorinated 3-methyl-PX was synthesized from 3-methyldiphenylether. For comparison purposes, toluene was chlorinated generally similarly to the manner in Examples 14, 15 and 17. The results are shown in Table 6.

TABLE 6

| | Main Catalyst Component Compounds | ppm | Co-catalyst Compounds | Average Chlorine Content | ppm | Chlorination Reaction Temp. °C. | Chlori-nation Degree | Composition of Reaction Liquid % Toluene | OCT | PCT | Dichloro-toluene | PCT/Mono chloroto-lene % |
|---|---|---|---|---|---|---|---|---|---|---|---|---|
| Example 14 | SbCl₅ | 500 | Chlorinated 3,6,9-Trimethyl-8-chloro-PX | 3.1 | 500 | 35 | 0.98 | 2.1 | 41.5 | 56.1 | 0.3 | 57.5 |

TABLE 6-continued

| | Main Catalyst Component | | Co-catalyst | Average Chlorine Content | ppm | Chlorination Reaction | | | | | | |
|---|---|---|---|---|---|---|---|---|---|---|---|---|
| | | | | | | Temp. °C. | Chlorination Degree | Composition of Reaction Liquid % | | | | PCT/Mono chlorotoluene % |
| | Compounds | ppm | Compounds | | | | | Toluene | OCT | PCT | Dichlorotoluene | |
| Example 15 | SbCl$_5$ | 500 | Chlorinated 3,6,9-Trimethyl-8-chloro-PX | 3.1 | 500 | 20 | 0.99 | 1.0 | 39.1 | 59.1 | 0.3 | 60.4 |
| Example 16 | SbCl$_3$ | 500 | Chlorinated 3,6,9-Trimethyl-8-chloro-PX | 2.0 | 500 | 20 | 0.94 | 6.2 | 36.8 | 56.8 | 0.2 | 60.7 |
| Example 17 | FeCl$_3$ | 500 | Chlorinated 3,6,9-Trimethyl-8-chloro-PX | 2.2 | 500 | 35 | 0.98 | 2.4 | 43.7 | 53.5 | 0.4 | 55.0 |
| Comparative Example 17 | SbCl$_5$ | 500 | Chlorinated 3-Methyl-PX | 4.9 | 500 | 35 | 0.97 | 3.5 | 43.2 | 53.0 | 0.3 | 55.1 |
| Comparative Example 18 | SbCl$_5$ | 500 | Chlorinated 3-Methyl-PX | 4.9 | 500 | 20 | 0.95 | 4.7 | 41.3 | 53.9 | 0.1 | 56.6 |
| Comparative Example 19 | FeCl$_3$ | 500 | Chlorinated 3-Methyl-PX | 4.9 | 500 | 40 | 0.99 | 1.4 | 46.1 | 51.8 | 0.7 | 52.9 |

It is apparent from the results shown in Table 6 that the co-catalysts according to this invention give improved results over those disclosed by Japanese Patent Application No. 1350/1980 (Japanese Patent Laid-Open Publication No. 110630/1981). It is further found that the selectivities to PCT of the co-catalysts according to this invention are appreciable when they are used for chlorinating toluene under the temperature conditions of lower range.

Although the present invention has been described with reference to the specific examples thereof, it should be understood that various modifications and variations can be easily made by those skilled in the art without departing from the spirit of the invention. It is intended to include all such modifications and variations within the wide scope of the invention as defined in the appended claims.

What is claimed is:

1. In the process for the nuclear chlorination of toluene wherein toluene is reacted with chlorine gas in the presence of a Lewis acid as a catalyst, the improvement which consists of adding as a cocatalyst at least one phenoxthine derivative which is a member selected from the group consisting of 3,9-dimethyl-6,8-dichlorophenoxthine, 3,9-dimethyl-2,6,8-trichlorophenoxthine, 1,3,9-trimethyl-6,8-dichlorophenoxthine, 1,3,9-trimethyl-2,6,8-trichlorophenoxthine, 1,9-dimethyl-6,8-dichlorophenoxthine, 1,9-dimethyl-2,6,8-trichlorophenoxthine, 6,9-dimethyl-2,8-dichlorophenoxthine, 3,6,9-trimethyl-8-chlorophenoxthine, 1,3,6,9-tetramethyl-8-chlorophenoxthine, 1,6,9-trimethyl-8-chlorophenoxthine and highly chlorinated derivatives thereof obtained by chlorinating said phenoxthine derivatives.

2. The process according to claim 1, wherein said co-catalyst consists of at least one compound selected from the group consisting of 3,9-dimethyl-2,6,8-trichlorophenoxthine and highly chlorinated derivatives thereof.

3. The process according to claim 1, wherein said co-catalyst consists of at least one compound selected from the group consisting of 1,3,9,trimethyl-6,8-dichlorophenoxthine and highly chlorinated derivatives thereof.

4. The process according to claim 1, wherein said co-catalyst consists of at least one compound selected from the group consisting of 3,9-dimethyl-6,8-dichlorophenoxthine and highly chlorinated derivatives thereof.

5. The process according to claim 1, wherein said co-catalyst consists of at least one compound selected from the group consisting of 3,6,9-trimethyl-8-chlorophenoxthine and highly chlorinated derivatives thereof.

6. The process according to claim 1, wherein said co-catalyst consists of at least one compound selected from the group consisting of 6,9-dimethyl-2,8-dichlorophenoxthine and highly chlorinated derivatives thereof.

7. The process according to claim 1, wherein said co-catalyst consists of at least one compound selected from the group consisting of 1,3,6,9-tetramethyl-8-chlorophenoxthine and highly chlorinated derivatives thereof.

8. The process according to claim 1, wherein aid co-catalyst consists of a mixture of highly chlorinated derivatives of 1,3,9-trimethyl-6,8-dichlorophenoxthine and highly chlorinated derivatives of 3,9-dimethyl-2,6,8-trichlorophenoxthine.

9. The process according to claim 1, wherein said co-catalyst consists of a mixture of highly chlorinated derivatives of 6,9-dimethyl-2,8-dichlorophenoxthine and highly chlorinated derivatives of 1,3,6,9-tetramethyl-8-chloro-phenoxthine.

10. The process according to claim 1 which is carried at a temperature of 0°–40° C.

* * * * *